United States Patent [19]

Neuber et al.

[11] Patent Number: 5,043,493
[45] Date of Patent: Aug. 27, 1991

[54] PROCESS FOR THE PREPARATION OF 2-CHLORO- OR 2-BROMO-NAPHTHALENE

[75] Inventors: marita Neuber, Frankfurt am Main; Ernst I. Leupold, Neu-Anspach, both of Fed. Rep. of Germany

[73] Assignee: Hoechst Aktiengesellschaft, Frankfurt am Main, Fed. Rep. of Germany

[21] Appl. No.: 547,455

[22] Filed: Jul. 3, 1990

[30] Foreign Application Priority Data

Jul. 5, 1989 [DE] Fed. Rep. of Germany ....... 3922035

[51] Int. Cl.$^5$ ............................................. C07C 17/24
[52] U.S. Cl. .................................................. 570/202
[58] Field of Search ....................................... 570/202

[56] References Cited

U.S. PATENT DOCUMENTS

| | | | |
|---|---|---|---|
| 4,368,339 | 1/1983 | Tada et al. | 570/202 |
| 4,806,697 | 2/1989 | Rule et al. | 570/202 |
| 4,806,698 | 2/1989 | Rule et al. | 570/202 |
| 4,935,561 | 6/1990 | Eiechler et al. | 570/202 |

FOREIGN PATENT DOCUMENTS

| | | | |
|---|---|---|---|
| 0062261 | 10/1982 | European Pat. Off. | |
| 164045 | 12/1985 | European Pat. Off. | 570/202 |

OTHER PUBLICATIONS

S. N. Borisov et al., "Acetoxysiloxane Oligomers—I. The Interaction of Acetic Anhydride with Cyclic Dimethylsiloxanes", Journal of Organometallic Chemistry., vol. II, (1968, pp. 27–33).

N. N. Vorozhtsov, Jr. et al., "Catalytic Conversion of Halogen Derivatives in the Aromatic Series", *J. Gen. Chem. (USSR)*, vol. 24, (1954), pp. 667–672.

J. P. Wibaut, F. L. J. Sixma and J. F. Suyver, "The Bromination of Naphthalene III", Rec. Trav. Chim., vol. 68, (1949), pp. 525–546.

*Primary Examiner*—Werren B. Lone

[57] ABSTRACT

Process for the preparation of 2-chloro- or 2-bromonaphthalene by isomerizing 1-chloro- or 1-bromonaphthalene over a zeolite as a catalyst which, in the anhydrous and template-free form, has the general formula (A)

$$Z \cdot Al_2O_3 \cdot x \, SiO_2 \qquad (A)$$

in which Z deontes $$M_2^I O, \ M^{II} O \ \text{or} \ (M^{III})_2 O_3,$$

in which $M^I$ represents an alkali metal atom or ammonium or a hydrogen atom, $M^{II}$ represents an alkaline earth metal atom and $M^{III}$ represents a rare earth metal of atomic number 57 to 71 in the Periodic Table of the Elements, and x denotes a number from 4 to 4,000, with the proviso that if Z represents $M_2^I O$, at least some of the alkali metal atoms are replaced by hydrogen atoms, ammonium and/or the other metal atoms mentioned.

13 Claims, No Drawings

PROCESS FOR THE PREPARATION OF 2-CHLORO- OR 2-BROMO-NAPHTHALENE

Description

The present invention relates to an improved and advantageous process for the preparation of 2-chloro- or 2-bromonaphthalene by zeolite-catalyzed isomerization of 1-chloro- or 1-bromonaphthalene. Intermediate products for the preparation of pharmaceuticals or aromatic monomers for polyesters can be obtained from 2-chloro-and 2-bromonaphthalene.

It is known that 1-chloronaphthalene can be isomerized to 2-chloronaphthalene in the liquid phase with the aid of $AlCl_3$ (L. Roux, Bull. Soc. Chim. 45, 510/521 (1886); and T. L. Jacobs et al., J. Org. Cnem. 11, 27/33 (1946)) or in the gas phase over solid catalysts, such as aluminum oxide or amorphous aluminosilicate (N. N. Vorozhtsov, Jr. and A. M. Beskin, J. Gen. Chem. USSR, 24, 667/672 (1954) English edition). Likewise the isomerization of 1- to 2-bromonaphthalene in the liquid phase (L. Roux, Bull. Soc. Chim. 45, 510/521 (1886) and J. P. Wibaut et al., Rec. Trav. Chim. 68, 525/546 (1949)) and in the gas phase over silica gel (F. Meyer and R. Schiffner, Ber. 65, 67/69 (1934)) and over $FeCl_3$ (J. P. Wibaut et al., Rec. Trav. Chim. 68, 525/546 (1949)) has been described.

However, these processes mentioned have considerable disadvantages. For example, if $AlCl_3$ is used, large amounts have to be employed for the isomerization reaction to proceed (for example 1.8 mol of $AlCl_3$ per mol of 1-chloronaphthalene). During work up the catalyst is destroyed and the salts formed have to be disposed of. Although the formation of tarry products can be limited if mild reaction conditions are chosen, gaseous HCl or HBr then has to be passed through the reaction mixture. HBr is also used as the carrier gas for the isomerization of 1-bromonaphthalene in the gas phase over $FeCl_3$ on pumice. At higher temperatures, the catalyst decomposes. In the isomerization of 1-chloronaphthalene over amorphous aluminosilicate at 400° C., the catalyst is deactivated very rapidly if the reaction is carried out without a carrier gas or with $CO_2$. The deactivation can be slowed down if HCl is used as the carrier gas. An HCl atmosphere is a requirement for aluminum oxide catalysts, so that the isomerization reaction can proceed.

There was thus a need for an improved process for the preparation of 2-chloro- or 2-bromonaphthalene which is distinguished in particular by long catalyst lives, by a good capacity of the catalyst for regeneration and by an industrially simple procedure in a non-corrosive atmosphere.

It has now been found that 2-chloro- and 2-bromonaphthalene can be prepared in an advantageous manner taking into account the abovementioned desirable aspects by isomerizing 1-chloro- or 1-bromonaphthalene over a zeolite as a catalyst which, in the anhydrous and template-free form, has the general formula (A)

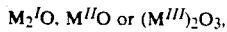   (A)

in which Z denotes

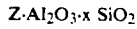

in which $M^I$ represents an alkali metal atom, ammonium or a hydrogen atom, $M^{II}$ represents an alkaline earth metal atom and $M^{III}$ represents a rare earth metal of atomic number 57 to 71 in the Periodic Table of the Elements, preferably cerium or lanthanum, and x denotes a number from 4 to 4,000, with the proviso that, if Z represents $M_2^I O$, at least some of the alkali metal atoms are replaced by hydrogen atoms, ammonium and/or the other metal atoms mentioned.

Suitable catalysts are zeolites as defined above, the pore openings of which are bounded by 10 or 12 tetrahedral atoms and which have a spaciousness index (SI) > 1. The spaciousness index is determined from the ratio of the rates of formation of n- and i-butane on the hydrocracking of a $C_{10}$-naphthene over the bifunctional form of the zeolite and is a measure of the effective pore width of the zeolite (J. Weitkamp et al., Appl. Catal. 27, 07/210 (1986)). Zeolites having a spaciousness index of between 3 and 18, such as, for example, the zeolites ZSM-12, EU-1 and beta, are particularly suitable.

Examples of zeolites which can be employed in the process according to the invention are the following:

zeolite EU-1 (HEU-1 denotes the proton form of this zeolite), described in European Patent 0,042,226;

zeolite ZSM-12 (HZSM-12 denotes the proton form of this zeolite), described in U.S. Pat. No. 3,970,544;

zeolite beta (H beta denotes the proton form of this zeolite), described in U.S. Pat. No. 3,308,069;

zeolite Y (HY denotes the proton form of this zeolite), described by D. W. Breck in "Zeolite Molecular Sieves", John Wiley & Sons, Inc., New York, London, Sydney and Toronto, 1974. (The spaciousness index of this zeolite is 21).

The zeolites mentioned can be prepared by hydrothermal synthesis in accordance with methods from the literature. After crystallization, the zeolites are filtered off, dried and calcined in an oxidizing atmosphere, preferably in air, in order to remove the organic template from the pores. (The template-free form is free from alkylammonium or phosphonium ions and from amines.)

The isomerization can be carried out either in the gas phase or in the liquid phase, isomerization in the gas phase being preferred. The reaction temperatures are between about 200° and about 600° C., preferably between about 300° and about 400° C. For the isomerization of 1-bromonaphthalene, somewhat lower temperatures than for the isomerization of 1-chloronaphthalene are advantageous under these conditions. The pressure is of little significance for the course of the reaction It can be adjusted to values of between about 0.5 and about 100 bar, preferably between about 1 and about 10 bar. The reaction is advantageously carried out under atmospheric pressure.

If the isomerization is carried out in the gas phase, the catalyst can be incorporated into the reactor in the form of pellets which contain a binder material, such as, for example, $Al_2O_3$ or $SiO_2$, or which are pressed without a binder. In this case, the 1-chloro- or 1-bromonaphthalene can be passed over the catalyst by itself or as a mixture with hydrogen, nitrogen or another gas which is inert in respect of the reaction participants The use of hydrogen as the carrier gas is advantageous.

The residence time of the reactants can be between about 0.1 and about 20 seconds, preferably between about 1 and about 10 seconds.

Any alkali metal ions present (Z in formula (A) in this case represents $M_2^IO$) are then replaced by di- or trivalent ions of the alkaline earth metals or rare earth metals or by ammonium ions or protons by ion exchange This acidic modification is necessary because the zeolite otherwise displays no catalytic action. It is advantageous here for at least 50%, preferably at least 75%, of the alkali metal ions to be replaced by the other ions mentioned. The zeolites are converted into the catalytically active form by dehydration (and removal of ammonium in the case of $NH_4^+$ forms) at 200° to 800° C., preferably at 400° to 50° C. The Si/Al ratio of the zeolites can vary within a wide range of between 2 and 2,000 - depending on the type of zeolite. Si/Al ratios of between 10 and 150 are preferred. The crystallite size can be between about 0.01 and about 10 μm, preferably between about 0.1 and about 1μm.

Satisfactory conversions are achieved at a liquid hourly space velocity (LHSV) of between 0.1 and 5 $h^{-1}$, liquid hourly space velocities of between 0.5 and 2 $h^{-1}$ being particularly preferred.

The isomerization in the liquid phase, which proceeds better with 1-bromonaphthalene than with 1-chloronaphthalene, can most easily be carried out in a stirred kettle using suspended catalyst.

If the catalyst has been deactivated, it can be reactivated by simple regeneration in an oxidizing atmosphere, in particular air or air/nitrogen mixtures, at temperatures between about 350° and about 800° C., in particular between about 500° and about 600° C.

The isomerization of 1-chloro- or 1-bromonaphthalene can be carried out in all apparatuses which are suitable for reactions in the gas or liquid phase The isomerization in the gas phase is easiest to handle industrially in a fixed bed flow reactor. The reactants can be metered into the reactor in liquid form and vaporized there upstream of the catalyst bed, or converted into the gas phase by suitable measures upstream of the reactor and passed into the reactor in this form. The products are condensed downstream of the reactor.

The product mixture can be separated into the 1- and 2-halogenonaphthalene isomers by crystallization. Some of the 2-chloro- or 2-bromonaphthalene is first separated off by crystallization from a solvent, such as, for example, methanol or acetone. The mixture of the two isomers depleted in 2-halogenonaphthalene can be separated by further crystallization steps or recycled to the reactor and enriched again with the 2-isomer at the most to the equilibrium composition by isomerization of 1-halogenonaphthalene. At 400° C., about 44% of 1- and 56% of 2-chloronaphthalene are in equilibrium. The 2-halogenonaphthalene which has been precipitated can be further purified by one or more recrystallizations.

High conversions of 1-chloro- or 1-bromonaphthalene coupled with a long catalyst life can be achieved by the zeolites used according to the invention. The conversion of 1-chloronaphthalene over an amorphous aluminosilicate, in spite of an HCl atmosphere, dropped from 51 to 41% in the course of 4 hours (temperature 400° C., LHSV 0.2 $h^{-1}$, N. N. Vorozhtsov, Jr. and A. M. Beskin, J. Gen. Chem. USSR, 24, 667/672 (1954) English edition). In contrast, an HEU-1 zeolite converted 56% of 1-chloro-naphthalene after 1 hour and 41% after 7 hours in a hydrogen atmosphere at the same temperature but 2.5 times the LHSV. The selectivity for the isomerization of 1-chloronaphthalene over HEU-1 is very high and is more than 98% at reaction temperatures of between 300° and 400° C. Naphthalene above all is formed as a by-product by elimination of HCl. Less than 0.05% of dichloronaphthalenes is formed. In the reaction of 1-bromonaphthalene, however, transbromination to naphthalene and dibromonaphthalenes occurs. The selectivity for 2-bromo-naphthalene is nevertheless very high, at 95% at 350° C. and 50% conversion.

The process according to the invention is explained in more detail by the following examples without being limited to these.

Examples

The catalytic reactions were carried out in a fixed bed flow apparatus. The reactor was made of quartz glass and had an internal diameter of 40 mm. 1-Chloro- or 1-bromo-naphthalene were metered in as a liquid by means of injection pumps, combined with the carrier gas at the reactor inlet and vaporized in a vaporizer zone upstream of the catalyst bed. The product mixture was condensed downstream of the reactor and analyzed by gas chromatography at certain intervals of time. The catalyst was employed in the form of binder-free pressed tablets or of extrudates containing $SiO_2$ as a binder. The catalyst volume was 25 ml. Before the reaction, the zeolites were activated in situ at 550° C. for 2 hours in a stream of nitrogen. After the experiment, the zeolites were regenerated in air (v = 15 1/hour) at 550° C.

Some results of the catalytic conversion of 1-chloro- and 1-bromonaphthalene on various zeolites are summarized in the following Tables 1 and 2.

In all the experiments the LHSV was 0.5 $h^{-1}$. Hydrogen was used as the carrier gas (v = 8 1/hour, normal conditions).

A mixture which contained 91.8% of 1-chloronaphthalene (1-Cl-Np), 8.0% of 2-chloronaphthalene (2-Cl-Np) and 0.2% of naphthalene (Np) was employed for the isomerization of chloronaphthalene.

The 1-bromonaphthalene (1-Br-Np) employed had a purity of 98%.

TABLE 1

(Np denotes naphthalene; HEU-1 denotes the proton form of the zeolite EU-1, HZSM-12 denotes the proton form of the zeolite ZSM-12, H beta denotes the proton form of the zeolite beta and HY denotes the proton form of the zeolite Y)

| | Example | | | | | |
|---|---|---|---|---|---|---|
| | 1 | 2 | 3 | 4 | 5 | 6 |
| Zeolite | HEU-1 tablets | HEU-1 tablets | HEU-1 tablets | HZSM-12 extrudates, 21% of $SiO_2$ | H beta extrudates, 21% of $SiO_2$ | HY tablets |
| Temperature, °C. | 400 | 300 | 450 | 400 | 400 | 400 |
| Time, hours | 1   7 | 1   7 | 1   7 | 1   7 | 1   7 | 1   2 |
| Product composition, % | | | | | | |

TABLE 1-continued (Np denotes naphthalene; HEU-1 denotes the proton form of the zeolite EU-1, HZSM-12 denotes the proton form of the zeolite ZSM-12, H beta denotes the proton form of the zeolite beta and HY denotes the proton form of the zeolite Y)

| | Example | | | | | | | | | | | |
|---|---|---|---|---|---|---|---|---|---|---|---|---|
| | 1 | | 2 | | 3 | | 4 | | 5 | | 6 | |
| Np | 1.1 | 0.5 | 0.6 | 0.3 | 3.1 | 2.3 | 0.8 | 0.5 | 3.8 | 1.2 | 7.1 | 3.6 |
| 1-Cl-Np | 44.0 | 65.5 | 47.4 | 74.3 | 42.9 | 56.5 | 45.3 | 60.8 | 41.9 | 73.5 | 80.5 | 86.3 |
| 2-Cl-Np | 54.9 | 34.0 | 52.0 | 25.4 | 54.0 | 41.2 | 53.9 | 38.7 | 54.3 | 25.3 | 12.4 | 10.1 |
| 2-Cl-Np % Cl-Np | 55.5 | 34.2 | 52.2 | 25.5 | 55.7 | 42.2 | 54.3 | 38.9 | 56.4 | 25.6 | 13.3 | 10.5 |

TABLE 2

| | Example | | | | | |
|---|---|---|---|---|---|---|
| | 7 | | 8 | | 9 | |
| Zeolite | HEU-1 Tablets | | HEU-1 Tablets | | HY Tablets | |
| Temperature, °C. | 250 | | 350 | | 350 | |
| Time, hours | 1 | 3 | 1 | 3 | 1 | 2 |
| Product composition, % | | | | | | |
| Np | 5.8 | 1.4 | 5.5 | 1.6 | 15.2 | 3.3 |
| 1-Br-Np | 56.2 | 70.0 | 41.8 | 52.1 | 55.3 | 86.9 |
| 2-Br-Np | 37.8 | 28.4 | 51.8 | 45.6 | 28.5 | 9.2 |
| DBr-Np | 0.2 | 0.2 | 0.9 | 0.7 | 1.0 | 0.6 |

DBr-Np denotes dibromonaphthalenes

Example 10

20 g of 1-bromonaphthalene were heated at 270° C. with 0.5 g of pulverulent HEU-1 zeolite in a 50 ml two-neck flask equipped with a thermometer and reflux condenser for 7 hours, while stirring. The composition of the resulting product was: 0.2% of naphthalene, 84.9% of 1-bromonaphthalene, 14.7% of 2-bromonaphthalene and 0.2% of dibromonaphthalenes.

If an NaHEU-1 zeolite (containing 75% of H and 25% of Na), CaEU-1 zeolite or LaEU-1 zeolite is used instead of the HEU-1 zeolite and the procedure is otherwise as described in Example 10, a similar result is obtained.

We claim:

1. A process for the preparation of 2-chloro- or 2-bromo-naphthalene, which comprises isomerizing 1-chloro- or 1-bromonaphthalene over a zeolite as a catalyst which, in the anhydrous and template-free form, has the formula (A)

$$Z \cdot Al_2O_3 \cdot x \, SiO_2 \quad (A)$$

in which Z denotes

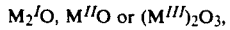

$$M_2^{I}O, \; M^{II}O \; \text{or} \; (M^{III})_2O_3,$$

in which $M^{I}$ represents an alkali metal atom or ammonium or a hydrogen atom, $M^{II}$ represents an alkaline earth metal atom and $M^{III}$ represents a rare earth metal of atomic number 57 to 71 in the Periodic Table of the Elements, and x denotes a number from 4 to 4,000, with the proviso that when Z represents $M_2^{I}O$, at least some of the alkali metal atoms are replaced by hydrogen atoms, ammonium or the other metal atoms mentioned or mixtures thereof.

2. The process as claimed in claim 1, wherein the effective pore width of the zeolite has a spaciousness index > 1.

3. The process as claimed in claim 1, wherein the effective pore width of the zeolite has a spaciousness index of about 3 to about 18.

4. The process as claimed in claim 1, wherein the isomerization is carried out in the gas phase.

5. The process as claimed in claim 1, wherein the isomerization is carried out in the liquid phase.

6. The process as claimed in claim 1, wherein the isomerization is carried out at temperatures of about 200° to about 600° C.

7. The process as claimed in claim 1, wherein the isomerization is carried out at temperatures of about 300° to about 400° C.

8. The process as claimed in claim 1, wherein the isomerization is carried out under atmospheric pressure.

9. The process as claimed in claim 1, wherein the isomerization is carried out under a pressure in the range of about 0.5 to about 100 bar.

10. The process as claimed in claim 1, wherein the isomerization is carried out under a pressure in the range of about 1 to about 10 bar.

11. The process as claimed in claim 1, wherein the 1-chloro- or 1-bromonaphthalene is passed over the zeolite catalyst in the absence of a gas which is inert towards the reactants.

12. The process as claimed in claim 1, wherein the 1-chloro- or 1-bromonaphthalene is passed over the zeolite catalyst as a mixture with a gas which is inert towards the reactants.

13. The process as claimed in claim 1, wherein 1-chloro- or 1-bromonaphthalene is passed over the zeolite catalyst as a mixture with hydrogen or nitrogen.

* * * * *